(12) United States Patent
Otsubo (10) Patent No.: US 7,028,841 B2
(45) Date of Patent: Apr. 18, 2006

(54) PACKAGED ASSEMBLY OF DISPOSABLE DIAPERS

(75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/686,811

(22) Filed: Oct. 17, 2003

(65) Prior Publication Data

US 2004/0134822 A1    Jul. 15, 2004

(30) Foreign Application Priority Data

Oct. 18, 2002    (JP) .............................. 2002-304965

(51) Int. Cl.
*B65D 71/06*    (2006.01)
(52) U.S. Cl. ................... 206/494; 604/385.01
(58) Field of Classification Search .............. 206/494, 206/497, 499, 812; 383/94, 106, 207, 209; 604/358, 385.01, 385.24, 385.25, 385.26, 604/385.3
See application file for complete search history.

(56) References Cited

U.S. PATENT DOCUMENTS

| | | | | |
|---|---|---|---|---|
| 4,661,102 A | * | 4/1987 | Shikata et al. | 604/385.25 |
| 4,966,286 A | * | 10/1990 | Muckenfuhs | 206/494 |
| 5,036,978 A | * | 8/1991 | Frank et al. | 206/494 |
| 5,054,619 A | * | 10/1991 | Muckenfuhs | 206/494 |
| 5,282,687 A | * | 2/1994 | Yee | 383/207 |
| 5,361,905 A | * | 11/1994 | McQueeny et al. | 206/494 |
| 5,934,470 A | * | 8/1999 | Bauer et al. | 206/494 |
| 5,967,665 A | * | 10/1999 | MacDonald et al. | 383/207 |
| 6,079,562 A | * | 6/2000 | Bauer et al. | 206/494 |
| 2002/0052588 A1 | | 5/2002 | Otsubo | |

FOREIGN PATENT DOCUMENTS

| | | | |
|---|---|---|---|
| JP | 47-36734 | * 12/1972 | |
| JP | 48-20638 | * 3/1973 | |
| JP | 50-21845 | * 3/1975 | |
| JP | 2002-035033 | * 2/2002 | |
| WO | WO 02/096333 | * 5/2002 | 604/385.01 |

\* cited by examiner

*Primary Examiner*—Luan K. Bui
(74) *Attorney, Agent, or Firm*—Lowe Hauptman & Berner, LLP (57) ABSTRACT

A package assembly includes a package and a plurality of disposable diapers. These diapers are compactly packed in a state of compression with the front and rear regions placed against one another in a back-and-forth direction. The diapers include first diapers that have the waist-surrounding end portions lying on the side of a top surface of package and second diapers that have the waist-surrounding end portions lying on the side of a bottom surface of the package. Both lateral portions of the crotch regions' bottom of the first and second diapers are folded inwardly of the respective diapers. In a row G formed by the diapers placed against one another in the back-and-forth direction, the number of the first diapers and the number of the second diapers are substantially equal to each other.

3 Claims, 9 Drawing Sheets

PACKAGED ASSEMBLY OF DISPOSABLE DIAPERS

BACKGROUND OF THE INVENTION

This invention relates to a packaged assembly of disposable diapers and more specifically, to a packaged assembly in which a plurality of disposable diapers are orderly packed within a package so that these diapers may be placed one upon another.

Japanese Patent Application Publication No. 2000-42028A discloses an example of the packaged assembly of disposable diapers and more specifically to a packaged assembly in which a plurality of pull-on disposable diapers each comprising a liquid-pervious topsheet, a liquid-impervious backsheet and a liquid-absorbent core disposed between these two sheets, in which the diapers are packed within the package so as to be placed one upon another in a back and forth direction with front and rear waist regions of each pair of the adjacent diapers being opposed to each other. Within the package, each of the diapers arranged in such manner to form a row has its waist's end portion lying on the side of the package's top surface and its crotch region's bottom lying on the side of the package's bottom surface.

In most of the disposable diaper, the liquid-absorbent core does not extend to the waist-surrounding end portions of the front and rear waist regions and therefore the remaining portion of the diaper except the waist-surrounding end portions has a thickness larger than that of those waist-surrounding end portions. Particularly when the crotch regions' bottom of the respective diapers are folded toward the respective rear waist regions to pack the diapers in the case of the above-cited Publication, the thickness of the remaining portions except for the waist-surrounding end portions will be remarkably larger than the thickness of these waist-surrounding end portions.

According to the packaged assembly as disclosed in the above-cited Publication, a total thickness of a row formed by a plurality of diapers placed one upon another in the back and forth direction is larger on the package's bottom space than on the side of the package's top surface. In other words, even if the diapers are packed so as to occupy the maximum dimension in the back and forth direction of the package on the side of the package's bottom surface, a gap will be left between each the waist-surrounding end portions of the diapers adjacent to each other and efficiency for packing the diapers into the package will be deteriorated. Furthermore, such well-known packaged assembly is inconvenient in that the waist's end portions of the diaper lying on the side of the package's top surface are readily bent when a plurality of the packages are stacked in a vertical direction. Consequently, a stability of such stack can not be expected and there is an anxiety that such stack of the packages might unintentionally collapse.

In addition, when two or more rows of the diapers are stacked within one and same package, the upper row of the diapers may flatten or collapse the waist-surrounding end portions of the diapers forming the lower row and form these waist-surrounding end portions of the diapers with a plurality of irregular wrinkles.

SUMMARY OF THE INVENTION

It is an object of this invention to provide a packaged assembly consisting of a package and a plurality of disposable diapers efficiently packed in a package without an anxiety that the packages might unintentionally collapse even when two or more packages are stack in a vertical direction.

According to the present invention, there is provided a packaged assembly of disposable diapers, comprising a package formed of a flexible sheet substantially in a rectangular hexahedron having first through sixth surfaces, each pair of the surfaces adjacent to each other being substantially orthogonal to each other and a plurality of pull-on disposable diapers, each including front and rear waist regions opposed to and connected with each other along transverse opposite lateral portions extending in a longitudinal direction in a vicinity of edges thereof so as to form a waist-hole and a pair of leg-holes, and each having a waist's end portion forming the waist-hole and a crotch region's bottom lying below the leg-holes wherein the plurality of diapers are compactly packed within the package so that the plurality of disposable diapers may have the respective waist regions placed in a state of compression one with another between opposed surfaces of the package.

The present invention is characterized by that each of the diapers is folded at both lateral portions of the crotch region's bottom along a pair of, fold-guiding lines each bifurcating from a transversely middle zone toward higher points of the leg-hole; and the package contains therein first diapers each having the waist's end portion lying on a side of the first surface of the package with respect to the crotch region's bottom and second diapers each having the waist's end portion lying on a side of the second surface of the package opposed to the first surface with respect to the crotch region's bottom so that the first and second diapers are alternately placed in close contact one with another to form a row in which the number of the first diapers is substantially equal to the number of the second diapers.

According to one preferred embodiment of the present invention, each of the diapers comprises a liquid-pervious topsheet facing a wearer's body, a liquid-impervious backsheet facing away from the wearer's body and a liquid-absorbent core interposed between the top- and backsheets and extending between the front and rear waist regions and wherein each of the diapers is further provided with a pair of second fold-guiding lines extending in the transversely opposite lateral portions in the longitudinal direction immediately outside transversely opposite side edges of the core so that the diaper are folded inwardly of the diaper at the transversely opposite lateral portions along the second fold-guiding.

According to another preferred embodiment of the present invention, a difference between the number of the first diapers and the number of the second diapers is in a range of 0 to ±3.

According to still another preferred embodiment of the present invention, the package contains therein at least two of the rows placed upon each other in a vertical direction.

According to further another preferred embodiment of the present invention, the package contains therein at least two of the rows arranged side by side.

DETAILED DESCRIPTION OF THE PREFERRED EMBODIMENTS

Details of the packaged assembly according to this invention will be more fully understood from the description given hereunder with reference to the accompanying drawings.

Figure 1:
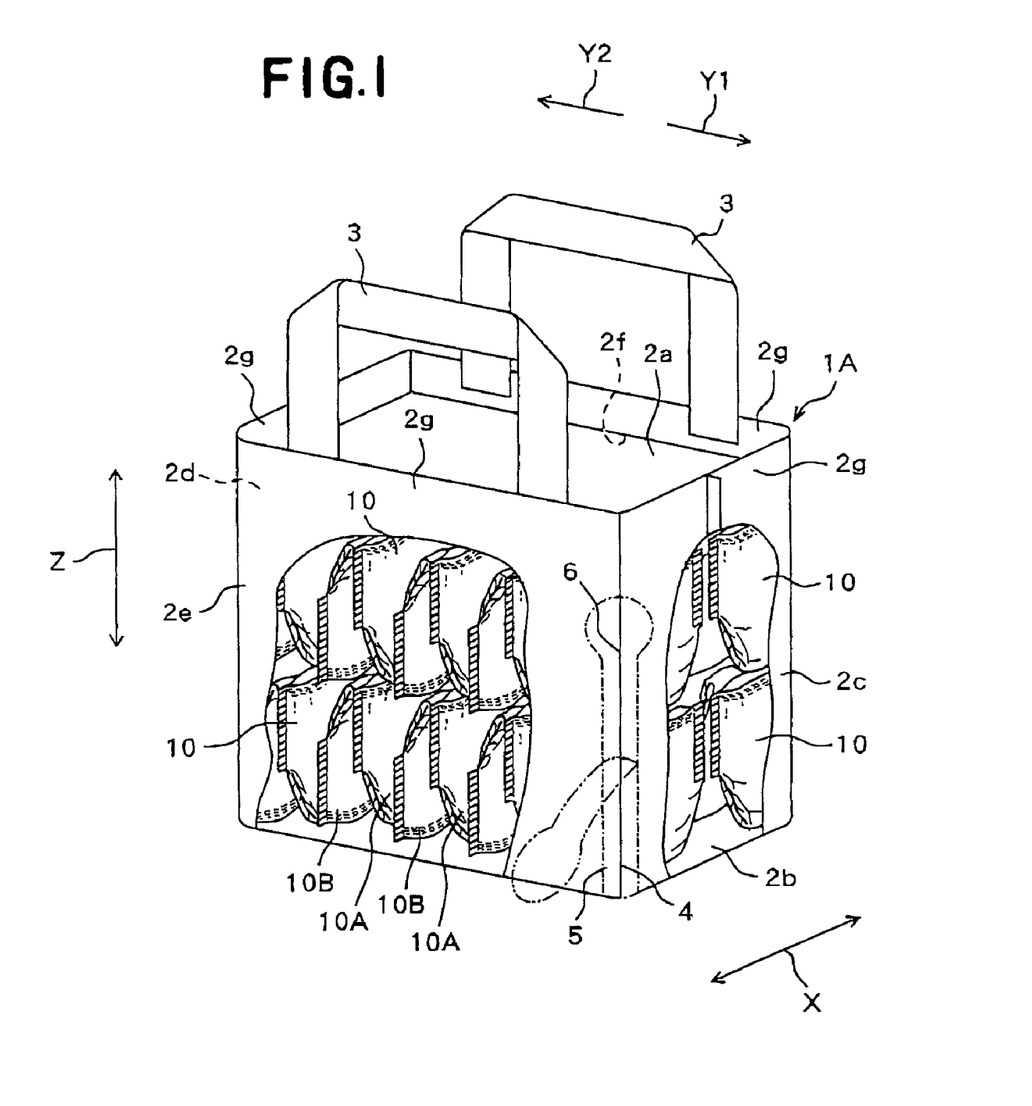
FIG. 1 is a partially cutaway perspective view showing a package.
Figure 2:
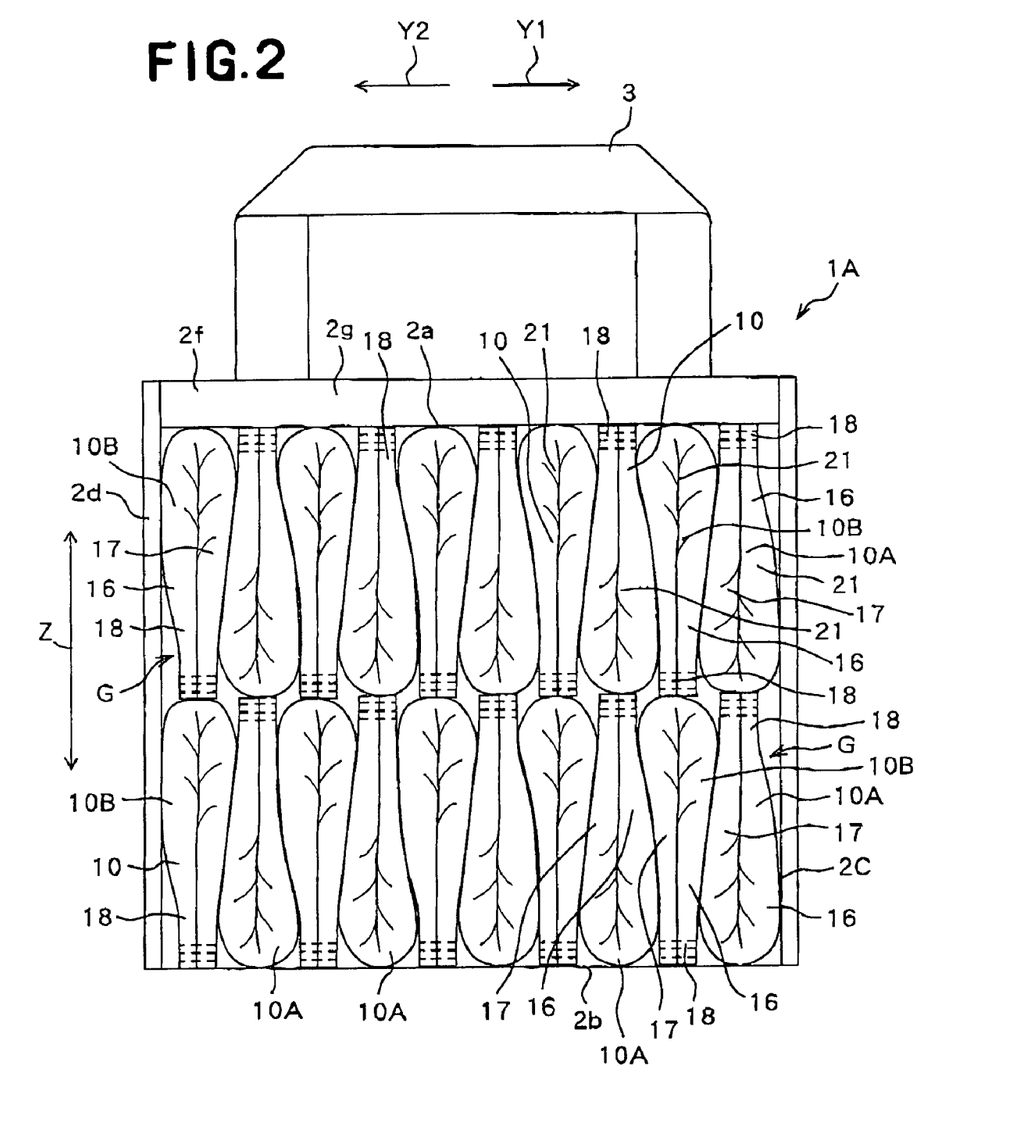
FIG. 2 is a side view showing the package as the diapers packed therein are exposed.
Figure 3:
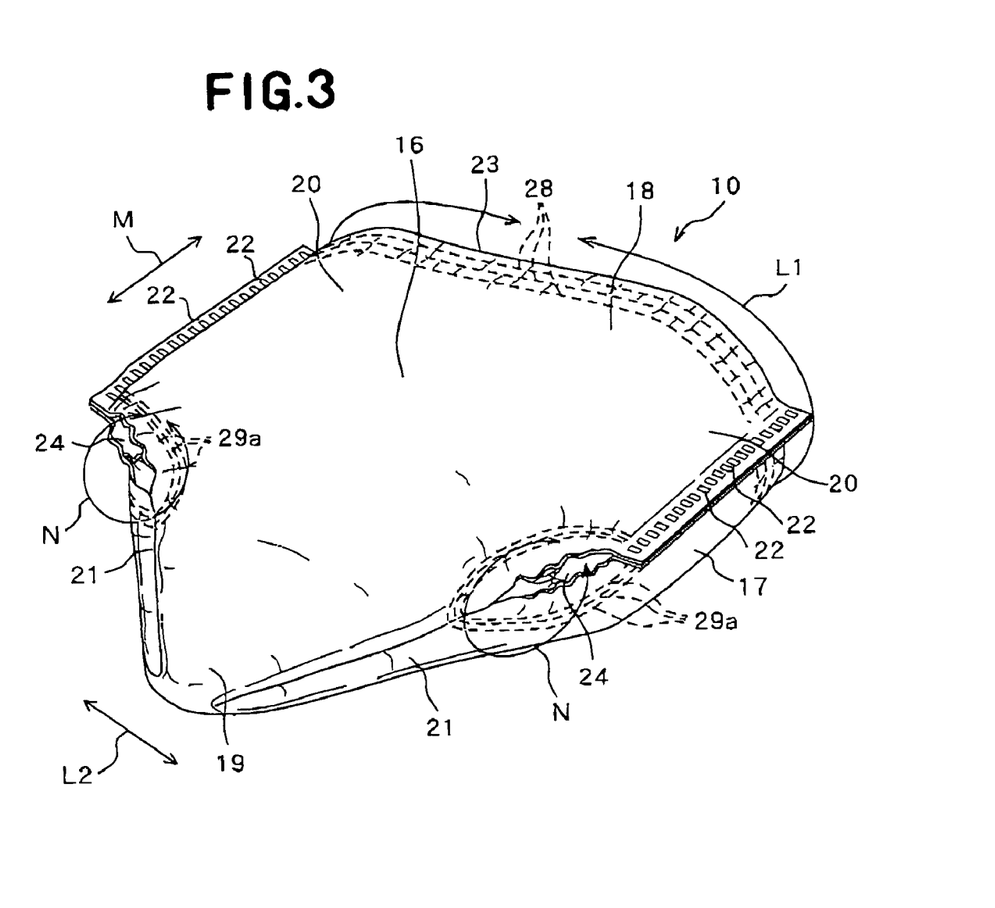
FIG. 3 is a perspective view showing a single diaper taken out from the package.
Figure 4:
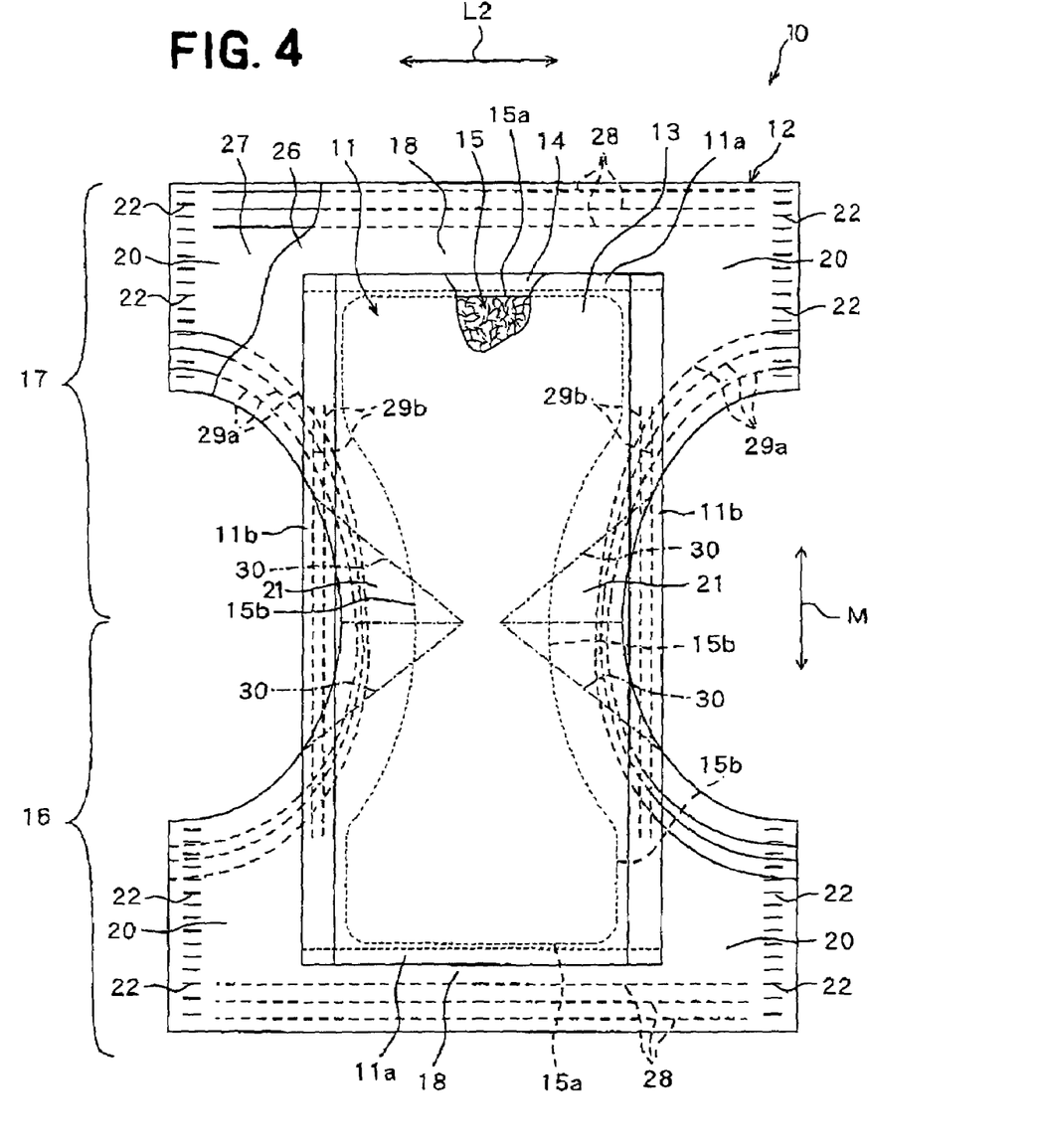
FIG. 4 is a partially cutaway developed plan view showing the diaper of FIG. 3.

FIG. 1 is a partially cutaway perspective view showing a package 1A, FIG. 2 is a side view showing the package 1A with a third side wall 2e cut away, FIG. 3 is a perspective view showing the individual diaper 10 taken out from the package 1A and FIG. 4 is a partially cutaway developed plan view showing the diaper 10 of FIG. 3 as front and rear waist regions disconnected from each other along respective waist's lateral portions 20. In FIGS. 1 and 2, a transverse direction is indicated by an arrow X, a forward direction as viewed in a back-and-forth direction of the package 1A is indicated by an arrow Y1, a backward direction as viewed in the back-and-forth direction is indicated by an arrow Y2 and a vertical direction is indicated by an arrow Z. In FIGS. 3 and 4, a waist-surrounding direction is indicated by an arrow L1 (in FIG. 3 alone) a width direction is indicated by an arrow L2, a longitudinal direction is indicated by an arrow M, and a leg-surrounding direction is indicated by an arrow N (in FIG. 3 alone).

This packaged assembly comprises the package 1A having a hexahedral shape of which each pair of surfaces adjacent to each other are substantially orthogonal to each other and the pull-on disposable diapers 10 orderly packed within the package 1A. In this packaged assembly, a plurality of the diapers 10 are compactly packed within the package 1A so as to placed one upon another in the back-and-forth direction (one direction) in a state of compression in this back-and-forth direction. Within this package 1A, ten diapers 10 are placed one upon another in the back-and-forward direction to form a row G and a pair of such rows G are placed side by side. Another pair of rows G placed side by side are stacked on the former pair of rows G. Thus a total of four rows G are packed within the package 1A.

The package 1A is formed by a flexible sheet and presents a substantially regular hexahedron which is relatively long in the back-and-forth direction. The package 1A is contoured by a substantially rectangular top surface (first surface) 2a and a bottom surface (second surface) 2b opposed to each other in the vertical direction, a substantially rectangular first lateral surface (third surface) 2c and a second lateral surface (fourth surface) 2d opposed to each other in the back-and-forth direction and a substantially rectangular third lateral surface (fifth surface) 2e and a fourth lateral surface (sixth surface) 2f opposed to each other in the transverse direction. These lateral surfaces 2c, 2d, 2e, 2f respectively have extended surfaces 2g rising upward from longitudinally opposite ends and transversely opposite side edges of the top surface 2a. The extended surfaces 2g associated with the third and fourth lateral surfaces 2e, 2f are provided with a pair of handling straps 3 describing circular arcs which are convex toward above the package L1. A corner 4 along which the first lateral surface 2c and the third lateral surface 2e intersect with each other is formed with perforations 5 arranged in the vertical direction as indicated by imaginary lines in FIG. 1. In the case of the package 1A, a region 6 surrounded by the perforations 5 so as to extend over parts of the first lateral surface 2c and the third lateral surface 2e may be torn off from the package 1A to form a dispensing port for the individual diapers 10 at this corner 4.

The diaper 10 comprises a liquid-impervious outer sheet 12 and a liquid-absorbent panel 11 placed on an inner side of the outer sheet 12. The diaper 10 has a front waist region 16 and a rear waist region 17 opposed to each other. The diaper 10 are folded so that the front and rear waist regions 16, 17 are overlaid and joined together along transversely opposite lateral portions 20 extending in the longitudinal direction by means of a plurality of welding lines 22 arranged intermittently in the longitudinal direction. The diaper 10 is formed with a waist-hole 23 and a pair of leg-holes 24. The diaper 10 has waist-surrounding end portions 18 extending in the waist-circumferential direction to form the waist-hole 23, leg-surrounding lateral portions 21 extending in the leg-circumferential direction to form the respective leg-holes 24 and a crotch region's bottom 19 lying below the leg-holes 24.

The outer sheet 12 (liquid-impervious backsheet) has an area larger than that of the panel 11 and presents a substantially hourglass-like planar shape. The outer sheet 12 comprises two hydrophobic fibrous nonwoven fabric layers 26, 27 placed upon each other. The panel 11 comprises, as will be seen in FIGS. 3 and 4, a rectangular liguid-pervious sheet 13 (liquid-pervious topsheet) facing a wearer's body, a rectangular liquid-impervious sheet 14 (liquid-impervious backsheet) facing away from the wearer's body and a liquid-absorbent core 15 interposed between these two sheets 13, 14 and bonded to respective inner surfaces of these sheets 13, 14. The sheets forming the panel 11 are bonded to the nonwoven fabric layers 26, 27 forming the outer sheet 12 by means of an adhesive (not shown). The core 15 extends from the crotch region's bottom 19 toward the waist-surrounding end portions 18. In the diaper 10, the core 15 is absent in the waist-surrounding end portions 18 and, in consequence, a thickness of the diaper 10 is larger in the region except for the waist-surrounding end portions 18 than in the waist-surrounding end portions 18.

The diaper 10 is formed with a pair of first fold-guiding lines 30 each bifurcating from a transversely middle zone of the crotch region's bottom 19 toward higher points of the associated leg-hole 24. As shown in FIG. 4, each of the first fold-guiding lines 30 substantially describes a V-shape extending between the transversely middle zone of the crotch region's bottom 19 and an edge of the associated leg-surrounding lateral portion 21. Both lateral portions of the crotch region's bottom 19 are folded along the first fold-guiding lines 30 inwardly of the diaper 10.

In this packaged assembly, first diapers 10A each having the waist-surrounding end portions 18 lying on the side of the top surface 2a of the package 1A with respect to the crotch region's bottom 19 and second diapers 10B each having the waist-surrounding end portions 18 lying on the side of the bottom surface 2b of the package 1A with respect to the crotch region's bottom 19 are alternately placed one upon another in the back-and-forth direction in the row G within the package 1A. The row G contains five of the first diaper 10A and five of the second diaper 10B. Thus, the number of the first diapers 10A is equal to the number of the second diapers 10B in the row G. In the row G, from the front side toward the backside in the back-and-forth direction, the front waist region 16 of the second diaper 10B lying immediately behind the first diaper 10A is placed against the rear waist region 17 of this first diaper 10A and the front waist region 16 of the first diaper 10A lying immediately behind this second diaper 10B is placed against the rear waist region 17 of this second diaper 10B.

In the case of this packaged assembly, the first diapers 10A and the second diapers 10B are alternately placed against one another and the number of the first diapers 10A is equal to the number of the second diapers 10B in the row G. Such construction of the row G advantageously ensures that the thickness of the row G in the back-and-forth direction has substantially no difference between its upper half and lower half in spite of the fact that, both in the first diapers 10A and in the second diapers 1013, the thickness of the region except for the waist-surrounding end portions 18 are larger than the thickness of the waist-surrounding end portion 18. Even when the diapers 10 are packed within the package 1A to fill the maximum dimension of the package 1A in the back-and-forth direction, no gap is formed between each pair of the diapers 10 adjacent to each other both in the upper half and in the lower half of the row G and thereby a packing efficiency for the diapers 10 within the package 1A can be improved.

In this packaged assembly, there is substantially no gap between each pair of the diapers 10 adjacent to each other both in the upper half and in the lower half of the row G, so the stability required when a plurality of the packages 1A are stacked in the vertical direction is reliably ensured. In another words, the overlying package 1A is reliably supported by the underlying package 1A and it is not likely that the stack of these packages 1A might unintentionally collapse.

In this packaged assembly, the first diapers 10 and the second diapers 10B are alternately placed against one another in the back-and-forth direction without leaving any gap and it is not likely that the waist-surrounding end portions 18 of the respective diapers 10 might be readily bent. Such manner of packaging allows two rows G of the diapers 10 to be stacked in the vertical direction without the anxiety that the upper row G of the diapers 10 might flatten or collapse the waist-surrounding end portions 18 of the diapers 10 in the underlying row G and these waist-surrounding end portions 18 of the diapers 10 might be formed with irregular wrinkles even when two rows G of the diapers 10 are stacked in the vertical direction within one and same package 1A.

The panel 11 has longitudinally opposite end portions 11a extending in the transverse direction and transversely opposite side edge portions 11b extending in the longitudinal direction. The end portions 11a of the panel 11 are defined by portions of the sheets 13, 14 extending outward beyond longitudinally opposite ends 15a of the core 15. Along the end portions 11a of the panel 11, the sheets 13, 14 are overlaid and have respective inner surfaces bonded together. The side edge portions 11b of the panel 11 are defined by portions of the sheet 13, 14 extending outward beyond side edges 15b of the core 15. Along the side edge portions 11b of the panel 11, the sheets 13, 14 are overlaid and have respective inner surfaces bonded together. In the vicinity of the waist-surrounding end portions 18, the side edge portions 11b of the panel 11 are folded back inwardly of the diaper 10 and bonded to the end portions 11a, respectively. Elastic members 29b extending in the longitudinal direction are attached to the side edge portions 11b of the panel 11 so that these elastic members 29b can contract in the longitudinal direction. The elastic members 29b are interposed between the sheets 13, 14 and bonded to respective the inner surfaces of these sheets 13, 14.

The waist-surrounding end portions 18 are defined by portion of the outer sheet 12 extending outward in the longitudinal direction beyond the longitudinally opposite end portions 11a of the panel 11. A plurality of waist-surrounding elastic members 28 extending in the waist-circumferential direction are attached to the waist-surrounding end portions 18 so that these elastic members 28 can contract in the waist-circumferential direction. These waist-surrounding elastic members 28 are interposed between the nonwoven fabric layers 26, 27 and bonded to these nonwoven fabric layers 26, 27. The transversely opposite lateral portions 20 are defined by portion of the outer sheet 12 extending outward in the transverse direction beyond the side edge portions 11b of the panel 11.

The leg-surrounding lateral portions 21 are defined by the side edge portions 11b of the panel 11 and the outer sheet 12. A plurality of leg-surrounding elastic members 29a extending in leg-circumferential direction are attached to the leg-surrounding lateral portions 21 so that these elastic D members 29a can contract in this leg-circumferential direction. The leg-surrounding elastic members 29a are interposed between the nonwoven fabric layers 26, 27 and bonded to these nonwoven fabric layers 26, 27.

To obtain the diaper 10 of FIG. 3 from the state shown in FIG. 4 in a plan view, the diaper 10 is folded in two along the crotch region's bottom 19 with the topsheet 13 inside so that the front and rear waist regions 16, 17 may be opposed to each other, then the front and rear waist regions 16, 17 are bonded together in the vicinity of the edges of the respective transversely opposite lateral portions 20 and finally the both leg-surrounding lateral portions 21 are folded along the first fold-guiding lines 30 inwardly of the diaper 10.

Though not illustrated, the elastic members 29a contract as the diaper 10 is shaped in the pants-type and, in consequence, the side edge portions 11b of the panel 11 rise above the topsheet 13. In this way, the side edge portions 11b of the panel 11 form barriers adapted to prevent bodily discharges from leaking outward beyond the side edge portions 11b of the panel 11.

Figure 5:
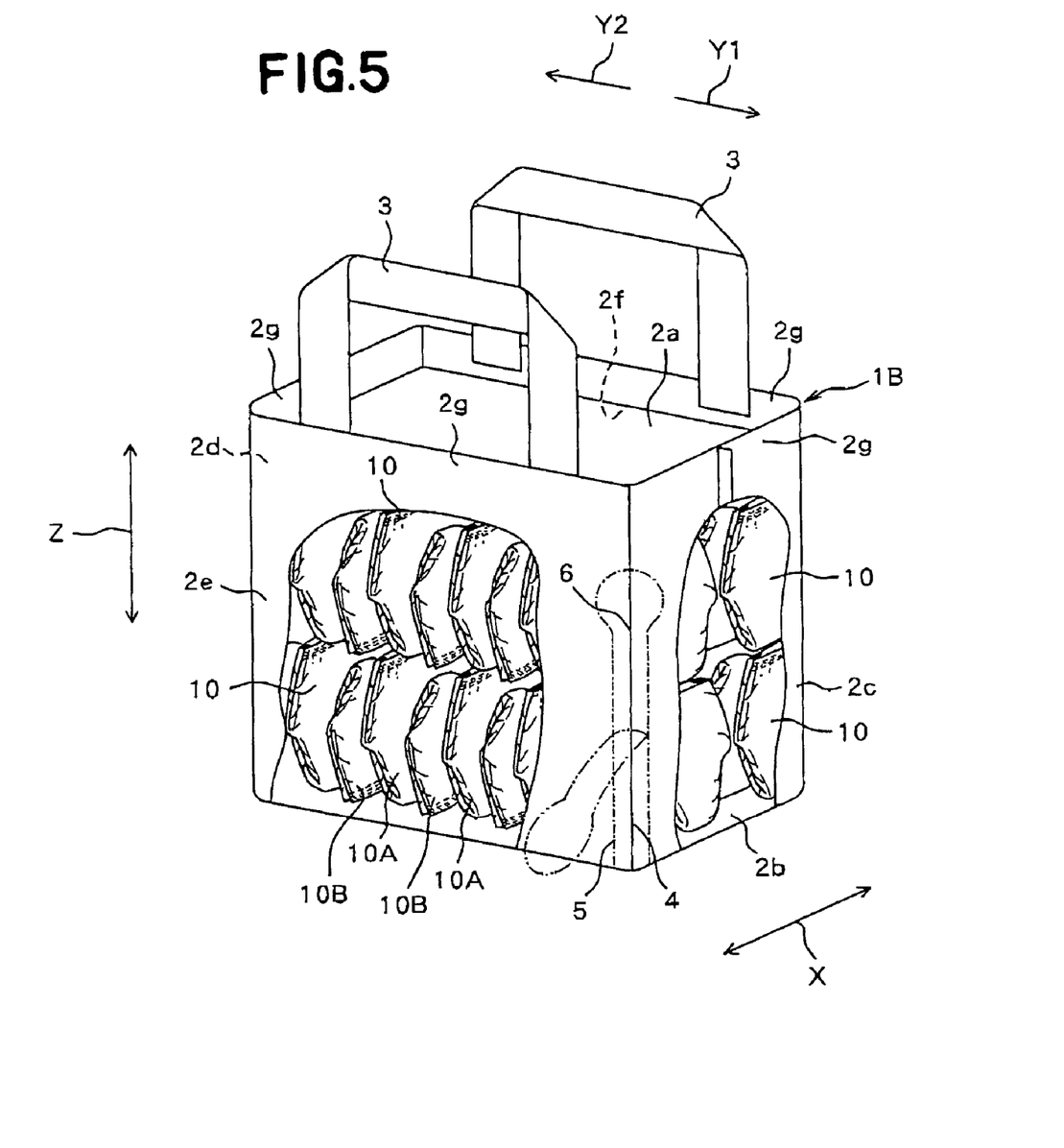
FIG. 5 is a partially cutaway perspective view showing another embodiment of the package.
Figure 6:
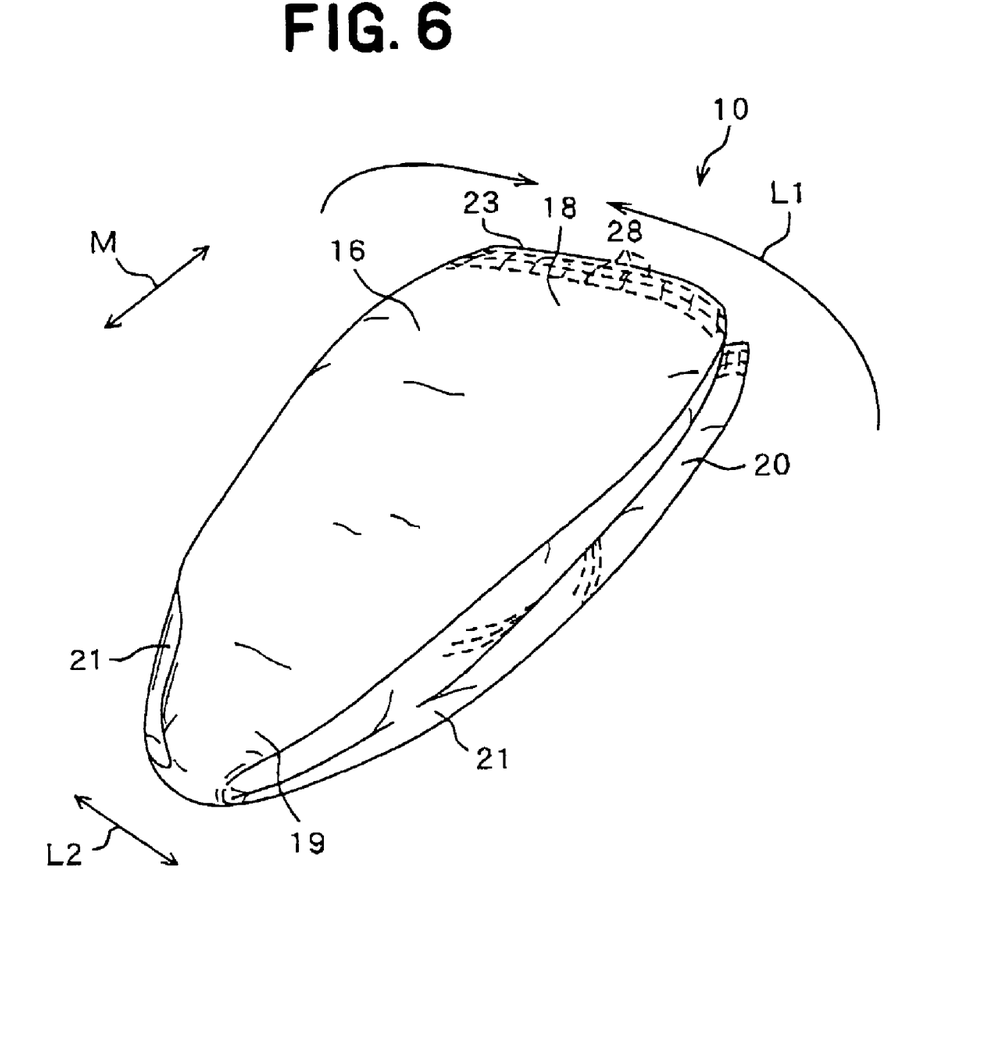
FIG. 6 is a perspective view showing a single diaper taken out from the package of FIG. 5.
Figure 7:
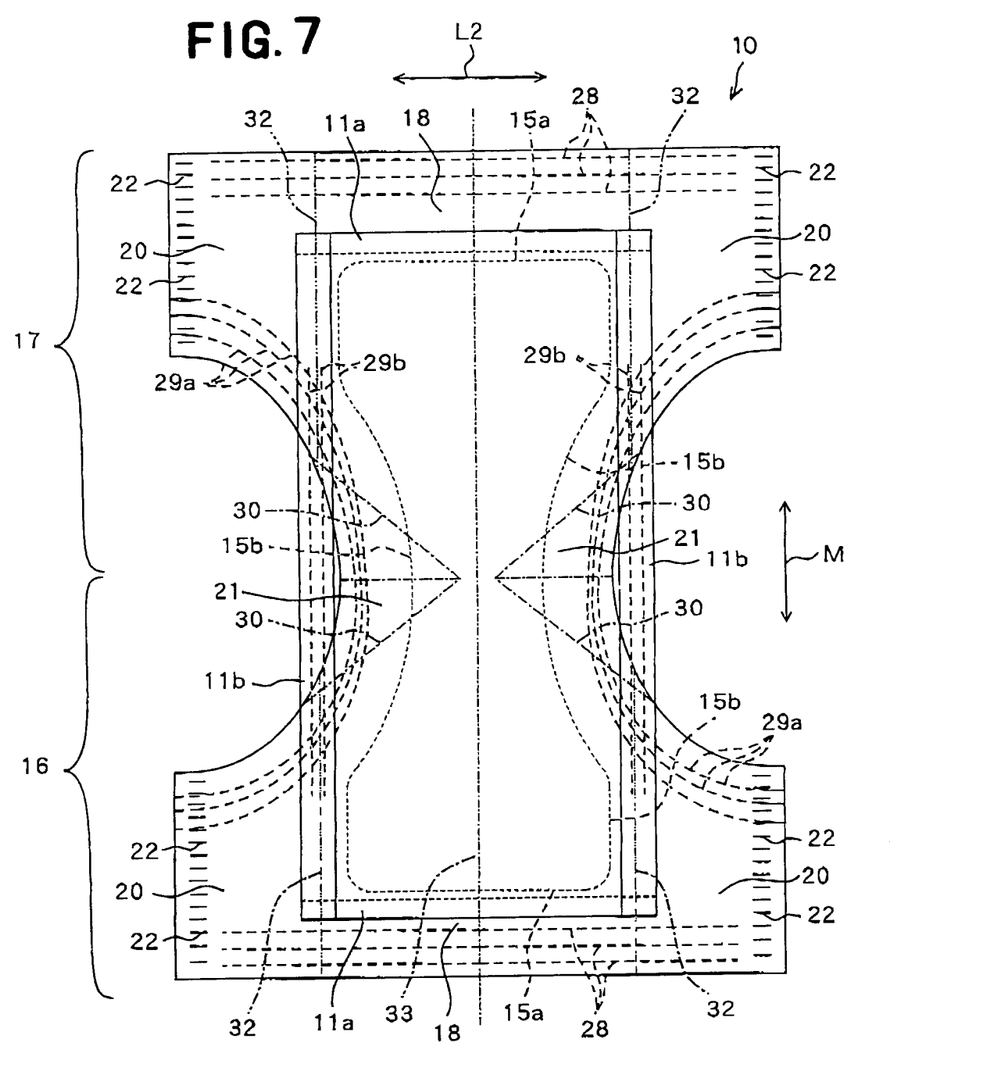
FIG. 7 is a developed plan view showing the diaper of FIG. 6.

FIG. 5 is a partially cutaway perspective view showing a package 1B according to another embodiment, FIG. 6 is a perspective view showing a single diaper 10 taken out from the package 1B and FIG. 7 is a developed plan view showing the diaper 10 of FIG. 6 as transverse opposite lateral portions 20 have been disconnected from each other. In FIG. 5, a transverse direction is indicated by an arrow X, a forward direction as viewed in a back-and-forth direction of the package 1B is indicated by an arrow Y1, a backward direction as viewed in the back-and-forth direction is indicated by an arrow Y2 and a vertical direction is indicated by an arrow Z. In FIGS. 6 and 7, a waist-surrounding direction is indicated by an arrow L1 (in FIG. 6 alone), a transverse direction is indicated by an arrow L2 and a longitudinal direction is indicated by an arrow M.

Similarly to the package 1A shown in FIG. 1, the packages 1B is formed of a flexible sheet substantially in a regular hexahedron which is relatively long in the back-and-forth direction, in which each pair of surfaces adjacent to each other are substantially orthogonal to each other. The diaper 10 to be packed within the package 1B is the pull-on disposable diaper 10 similar to that shown in FIG. 1. The packaged assembly according to this embodiment is distinguished from that of FIG. 1 in the arrangement as will be described.

The both lateral portions of the crotch region's bottom 19 are folded along the first fold-guiding lines 30 inwardly of the diaper 10 and the transverse opposite lateral portions 20 are folded along the second fold-guiding lines 32 inwardly of the diaper 10. The manner in which the crotch region's bottom 19 is folded is same as in the case of FIG. 3 and details thereof will not be described here again. As indicated by chain double-dashed lines in FIG. 7, second fold-guiding lines 32 extend immediately outside the transversely opposite side edges 15b of the core 15 parallel to a longitudinal center line 33 bisecting the width dimension defined between the transverse opposite lateral portions 20 so as to extend through these transverse opposite lateral portions 20 also in the longitudinal direction.

In this packaged assembly, the first diapers 10A packed within the package 1B with the waist-surrounding end portions 18 lying on the side of the top surface 2a relative to the crotch regions' bottoms 19 and the second diapers 10B packed within the package 1B with the waist-surrounding end portion 18 lying on the side of the bottom surface 2b relative to the crotch regions' bottoms 19 are alternately placed against one another in the back-and-forth direction (one direction). Within the package 1B, a total of ten diapers 10 placed one against another in the back-and-forth direction to form a row G in the manner similar to the case of the package 1A and two of such rows G placed side by side. Additional pair of such rows G placed side by side are stacked upon the former pair of the rows G. These diapers 10 are compactly packed within the package 1B between the first and second surfaces 2c, 2d in a state of compression exerted in the back-and-forth direction. The row G is formed by five of the first diapers 10A and five of the second diapers 10B. Namely, the number of the first diapers 10A is equal to the number of the second diapers 10B in the row G. In the row G, from the front side toward the backside in the back-and-forth direction, the front waist region 16 of the second diaper 10B lying immediately behind the first diaper 10A is placed against the rear waist region 17 of this first diaper 10A and the front waist region 16 of the first diaper 10A lying immediately behind this second diaper 10B is placed against the rear waist region 17 of this second diaper 10B.

In the case of this packaged assembly also, the first diapers 10A and the second diapers 10B are alternately placed against one another and the number of the first diapers 10A is equal to the number of the second diapers 10B in the row G. Such construction of the row G advantageously ensures that the thickness of the row G in the back-and-forth direction has substantially no difference between its upper half and lower half. This embodiment is characterized in that not only the transversely opposite lateral portions of the crotch region's bottom 19 but also the waist's lateral portions 20 are folded inwardly of the diaper 10. In this way, the diaper 10 can be made further compact in comparison to the diaper 10 of FIG. 3 and thereby the diapers 10 can be more efficiently packed within the package 1B.

Figure 8:
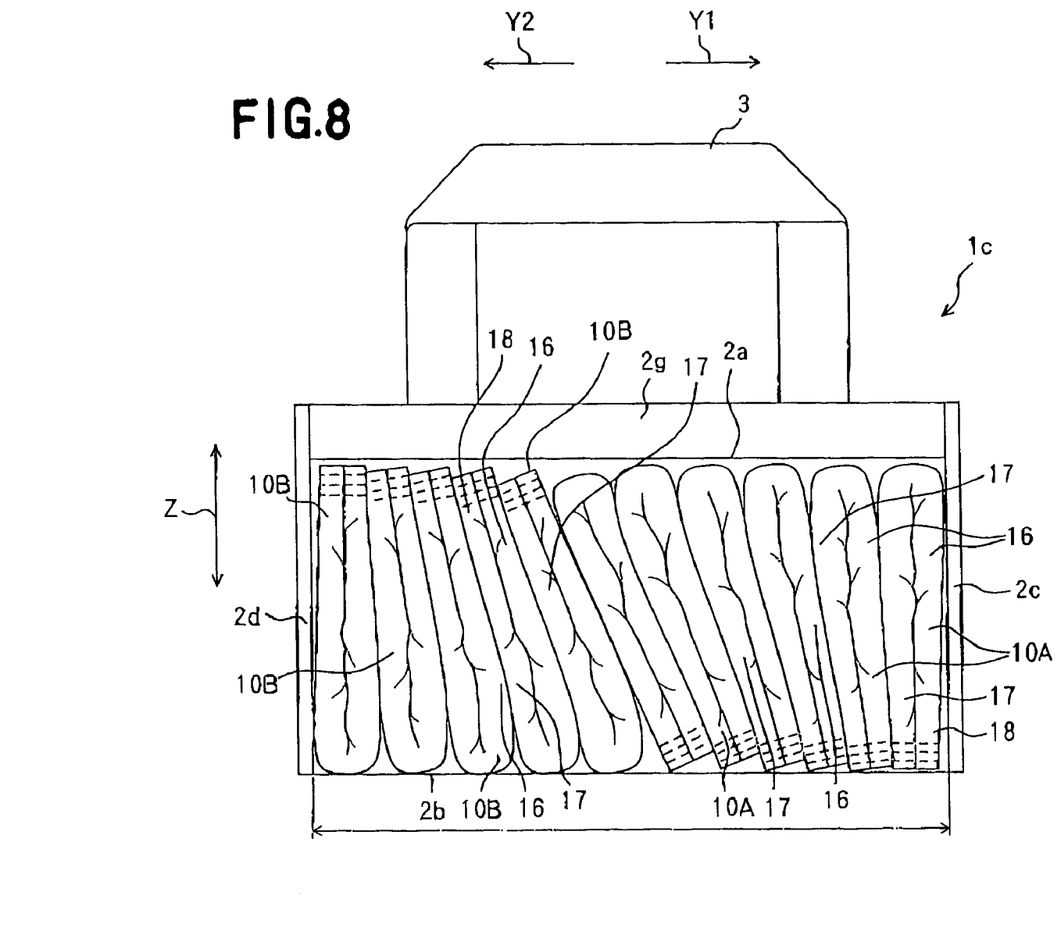
FIG. 8 is a partially cutaway side view showing still another embodiment of the package to expose the diapers packed therein.

In the case of the packaged assembly illustrated in FIG. 8, there is substantially no gap between each pair of the diapers 10 adjacent to each other both in the upper half and in the lower half of the row G, so the stability required when a plurality of the packages 1B are stacked in the vertical direction is reliably ensured and there is no anxiety that a stack of the packages 1B might unintentionally collapse. In this packaged assembly, the first diapers 10A and the second diapers 10B are alternately placed against one another in the back-and-forth direction without leaving any gap and it is not likely that the waist-surrounding end portions 18 of the respective diapers 10 might be readily bent and the upper row G of the diapers 10 might flatten or collapse the waist-surrounding end portions 18 of the diapers 10 in the underlying row G.

Figure 9:
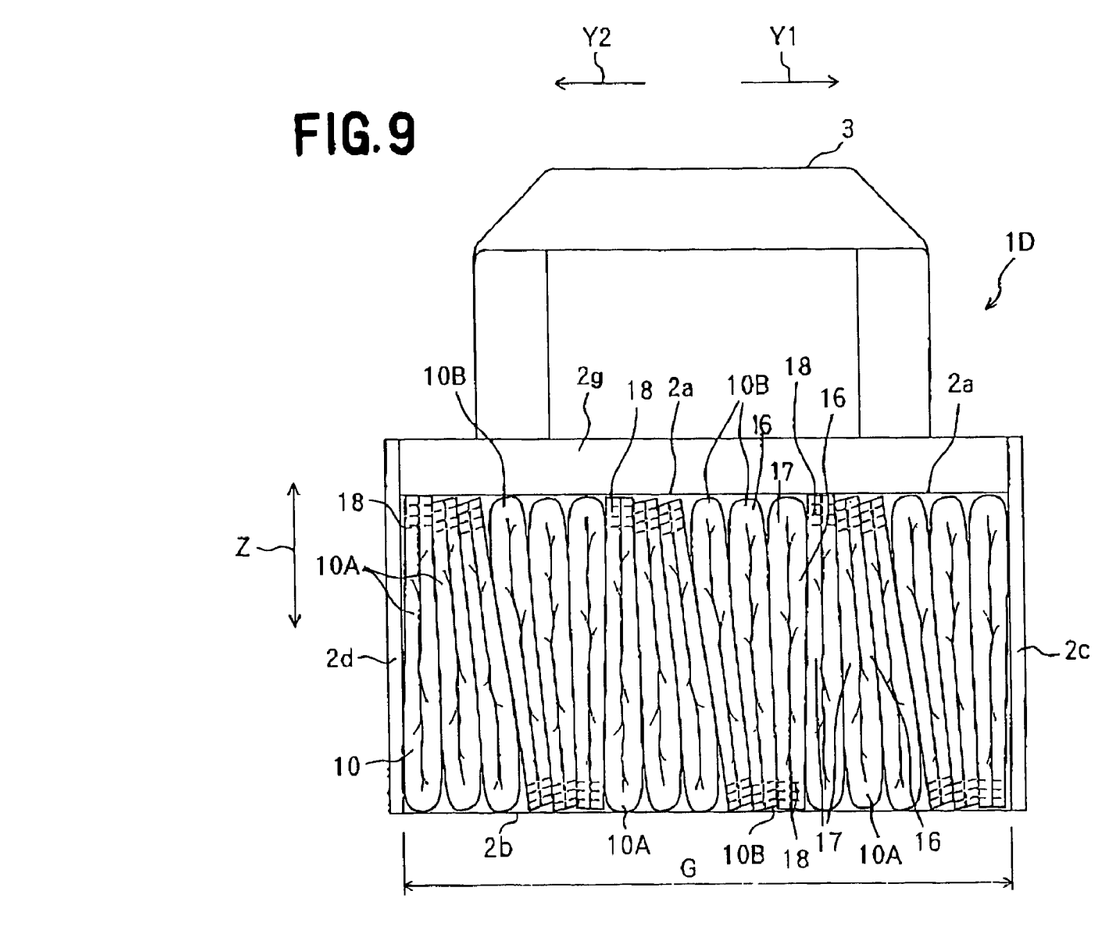
FIG. 9 is a partially cutaway side view showing further another embodiment of the package to expose the diapers packed therein.

FIG. 8 is a partially cutaway side view showing a package 1C according to another embodiment of the invention and FIG. 9 is a partially cutaway side view showing a package 1D according to further another embodiment of the invention. In FIGS. 8 and 9, a forward direction as viewed in a back-and-forth direction is indicated by an arrow Y1, a backward direction as viewed in a back-and-forth direction is indicated by an arrow Y2 and a vertical direction is indicated by an arrow Z.

Similarly to the package 1A shown in FIG. 1, the package 1C as well as the package 1D has a hexahedral shape which is relatively long in the back-and-forth direction and each pair of surfaces adjacent to each other are substantially orthogonal to each other. The disposable diapers 10 to be packed therein are of pants-type. The packages 1C, 1D are adapted to contain therein the diapers 10 each having the both lateral portions of the crotch region's bottom 19 folded along the first fold-guiding lines 30 inwardly of the diaper 10 as shown in rig. 3 or the diapers 10 each having the both lateral portions of the crotch region's bottom 19 folded along the first fold-guiding lines 30 inwardly of the diaper 10 and the transverse opposite lateral portions 20 folded along the second fold-guiding lines 32 inwardly of the diaper 10 as shown in FIG. 6.

In the case of the packaged assembly shown in FIG. 8, the package 1C contains therein a total of eleven diapers 10 placed against one another in the back-and-forth direction (one direction) in each row G. The row G is formed by five of the first diapers 10A and six of the second diapers 10B. In the row G, five of the first diapers 10A are serially arranged from the first lateral surface 2c to the longitudinally middle position of the package 1C and six of the second diapers 10B are serially arranged from the longitudinally middle position of the package 1C to the second lateral surface 2d. These diapers 10 are compactly packed within the package 1C so as to placed against one another in the back-and-forth direction in a state of compression in this back-and-forth direction. Within the package 1C, each of the first diapers 10A has its waist-surrounding end portion 18 lying on the side of the top surface 2a of the package 1C relative to its crotch region's bottoms 19 and each of the second diapers 10B has its waist-surrounding end portions 18 lying on the side of the bottom surface 2b of the package 1C relative to its crotch region's bottom 19.

The first diapers 10A are serially arranged from the first lateral surface 2c toward the longitudinally middle position of the package 1C in a manner that the front waist region 16 of the diaper 10A lying immediately behind the preceding diaper 10A is placed against the rear waist region 17 of this preceding diaper 10A and so on. The second diapers 10B are serially arranged from the longitudinally middle position of the package 1C in the same manner as the first diapers 10A.

In the case of the packaged assembly illustrated in FIG. 8, the number of the second diapers 10B is more than the number of the first diaper 10A by one. In spite of this difference, there is substantially no difference between a thickness dimension of the row G in the back-and-forth direction on the side of the top surface 2a of the package 1C and a thickness dimension of the row G in the back-and-forth direction on the side of the bottom surface 2b of the package 1C and there is no gap between each pair of the diapers 10 adjacent to each other both in the upper half and in the lower half of the row G. With an advantageous consequence, the diapers 10 can be packed within the package 1C with an improved efficiency. Furthermore, this packaged assembly ensures a high stability when a plurality of packages 1C are stacked in the vertical direction without any anxiety that the stack of the packages 1C might unintentionally collapse.

In the case of the packaged assembly illustrated in FIG. 9, the package 1D contains therein a row G consisting of eighteen diapers 10 serially placed against one another in the back-and-forth direction (one direction). Specifically, these eighteen diapers 10 consist of nine of the first diapers 10A and nine of the second diapers 10B. In the row G, each set of three first diapers 10A and each set of three second diapers 10B are alternately appear and all of these first and second diapers 10A, 10B are compactly packed within the package 1D between first and second lateral surfaces 2c, 2d of the package 1D in a state of compression exerted in the back-and-forth direction.

Each of the first diapers 10A has its waist-surrounding end portion 18 lying on the side of the top surface 2a of the package 1D relative to its crotch region's bottom 19. Each of the second diapers 10B has its waist-surrounding end portion 18 lying on the bottom surface 2b of the package 1D relative to its crotch region's bottom 19. Among each set of three first diapers 10A, the front waist region 16 of the diaper 10A lying immediately behind the preceding diaper 10A is placed against the rear waist region 17 of the preceding diaper 10A and so on. Among each set of three second diapers 10B also, the front waist region 16 of the diaper 10B lying immediately behind the preceding diaper 10B is placed against the rear waist region 17 of the preceding diaper 10B and so on. As for relationship between the first and second diapers 10A, 10B, the front waist region 16 of the second diaper 10B is placed against the rear waist region 17 of the first diaper 10A.

In the case of the packaged assembly illustrated in FIG. 9, the number of the first diapers 10A is equal to the number of the second diapers 10B and there is no difference in the thickness dimension of the grow G in the back-and-forth direction between on the side of the top surface 2a of the package 1D and on the side of the bottom surface 2b of the package 1D. Furthermore, there is substantially no gap between each pair of the diapers 10 adjacent to each other both in the upper half and in the lower half of the row G, so the diapers 10 can be packed within the package 1D with an improved efficiency. This packaged assembly is effective to improve the stability required when a plurality of the packages 1D are stack in the vertical direction and thereby to prevent the anxiety that a stack of the packages 1D might unintentionally collapse.

In the case of the packaged assembly illustrated in FIG. 9, it is also possible to alternately arrange a set of four or more first diapers 10A and a set of four or more second diapers 10B series so that the respective diapers may be placed against one another in the back-and-forth direction.

In these embodiments of the packaged assembly having been described and illustrated, a difference between the number of the first diapers 10A and the number of the second diapers 10B is preferably in a range of 0 to ±3. In these embodiments of the packaged assembly, three or more rows G of the diapers 10 may be stacked in the vertical direction and three of such stack maybe arranged side by side. The diaper to be packed within these packages 1A, 1B, 1C, 1D may be also open-type diaper of which the front and rear waist regions are connected to each other along the transversely opposite lateral portions 20 when the diaper is put on the wearer's body. It should be understood here that the number of the diapers 10 to be packed within the packages 1A, 1B, 1C, 1D is not particularly specified.

While the packages 1A, 1B, 1C, 1D have been described above on the basis of the assumption that the front surface is defined by the first lateral surface 2c and the back-and-forth direction is defined by the direction extending from the first lateral surface 2c toward the second lateral surface 2d, it is also possible to assume the third lateral surface 2e as the front surface, to assume the direction extending from this third lateral surface 2e toward the fourth lateral surface 2f as the back-and-forth direction and to assume the direction extending from the first lateral surface 2c toward the second lateral surface 2d as the transverse direction In this case, the diapers 10 are successively placed against one another from the third lateral surface 2e toward the fourth lateral surface 2f and the diapers 10 successively placed against one another between the third lateral surface 2e and the fourth lateral surface 2f form the row G. While the top surface 2a has been assumed as the first surface, the bottom surface 2b has been assumed as the second surface and the first through fourth lateral surfaces 2c, 2d, 2e, 2f have been assumed as the third through sixth surfaces, it is also possible that the first lateral surface 2c is assumed as the first surface, the second lateral surface 2d is assumed as the second surface, and the top surface 2a, the bottom surf ace 2b, the second lateral surface 2e and the fourth lateral surface 2f are assumed as the third through sixth surfaces, respectively. In this case, the diaper 10 will be stacked between the top surface 2a and the bottom surface 2b to form the row G.

The package 1A, 1B, 1C, 1D may be formed using a breathable but liquid-impervious plastic film or a breathable but liquid-impervious fibrous nonwoven fabric.

The liquid-pervious sheet 13 may be formed using a hydrophilic fibrous nonwoven fabric, hydrophobic fibrous nonwoven fabric having a plurality of fine pores or a plastic film having a plurality of fine pores. The liquid-impervious sheet 14 may be formed using a hydrophobic fibrous nonwoven fabric, a breathable but liquid-impervious plastic film, a composite nonwoven fabric consisting of two or more hydrophobic fibrous nonwoven fabric layers laminated one upon another or a composite sheet consisting of a hydrophobic fibrous nonwoven fabric and a breathable but liquid-impervious plastic film laminated upon each other. The outer sheet 12 may be formed using composite nonwoven fabric consisting of two or more hydrophobic fibrous nonwoven fabric layers laminated one upon another.

The fibrous nonwoven fabric used herein may be selected from the group consisting of those obtained by spun lace process, needle punch process, melt blown process, thermal bond process, spun bond process, chemical bond process and air-through process. Component fibers of the nonwoven fabric may be selected from the group consisting of polyolefine-, polyester-, polyamide-based fibers and core-sheath type or side-by-side type conjugated fibers of polyethylene/polypropylene or polyethylene/polyester.

The core 15 comprises a mixture of fluff pulp and super-absorbent polymer particles or a mixture of fluff pulp, super-absorbent polymer particles and thermoplastic synthetic resin fibers, in both cases, compressed to a desired thickness. Preferably, the core 15 is entirely wrapped with a liquid-pervious sheet such as a tissue paper or a hydrophilic fibrous nonwoven fabric in order to prevent the core 15 from getting out of its initial shape and/or to prevent the polymer particles from falling off. The polymer particles may be selected from the group consisting of starch-based polymer particles, cellulose-based polymer particles or synthetic polymer particles.

Bonding of the sheets 13, 14 to each other, bonding of the core 15 to the sheets 13, 14 and bonding of the elastic members 29b to the sheets 13, 14 may be achieved by use of a hot melt adhesive or welding means such as heat-sealing or ultrasonic sealing techniques.

The packaged assembly according to this invention is primarily characterized in that a plurality of diapers comprising the first and second diapers, each having the crotch region's bottom folded inwardly of the diaper, are densely packed between the opposed surfaces with the package and substantially same number of first and second diapers are successively placed against one another so as to form a row. With the packaged assembly according to the present invention, there is no gap between each pair of the diapers adjacent to each other both in the upper half and in the lower half of the row even when a plurality of diapers, each having a differential thickness dimension between the waist-surrounding end portion and the remaining portion, are packed to fill the maximum length of the package in one direction. In this way, the packing efficiency of the package for the diapers can be improved.

With this packaged assembly, there is no gap left between each pair of the diapers adjacent to each other both in upper half and in the lower half of the row and therefore a plurality of packages can be stably stacked in the vertical direction without the anxiety that the stack of packages might unintentionally collapse.

In this packaged assembly, the first and second diapers are closely placed against one another in the back-and-forth direction without leaving any gap between each pair of the diapers adjacent to each other and therefore, it is not likely that the waist-surrounding end portions of the diapers might be readily bent. Even when two or more rows are stacked in the vertical direction, there is no possibility that the overlying row of the diapers might flatten or collapse the waist-surrounding end portions of the diapers in the underlying row and consequently form the waist-surrounding end portions of the diapers in the underlying row(s) with a plurality of irregular wrinkles.

The packaged assembly in which not only the both lateral portions of the crotch regions' bottoms but also the waist-surrounding end portions of the first diapers as well as the second diapers are folded inwardly of the diapers when packed within the package further improves the packing efficiency of the package for the diapers.

With the packaged assembly in a difference between the number of the first diapers and the number of the second diapers is ±3 or less, there is left substantially no gap between each pair of the diapers adjacent to each other both in the upper half and in the lower half of the row even the number of the first diapers and the number of the second diapers in the row are different from each other. In this way, it is possible to achieve the same effect as the case in which the number of the first diapers and the number of the second diapers are equal to each other.

What is claimed is:

1. A packaged assembly of disposable diapers, comprising a package formed of a flexible sheet substantially in a rectangular hexahedron having first through sixth surfaces, each pair of said surfaces adjacent to each other being substantially orthogonal to each other; and a plurality of pull-on disposable diapers, each of said diapers including front and rear waist regions opposed to and connected with each other along transverse opposite lateral portions extending in a longitudinal direction in a vicinity of edges thereof so as to form a waist-hole and a pair of leg-holes, and each of said diapers having a waist's end portion forming said waist-hole and a crotch region's bottom lying below said leg-holes;

wherein said plurality of diapers are compactly packed within said package so that said plurality of disposable diapers may have the respective waist regions placed in a state of compression one with another between opposed surfaces of said package;

each of said diapers is folded at both lateral portions of said crotch region's bottom along a pair of fold-guiding lines each bifurcating from a transversely middle zone toward higher points of said leg-hole;

said package contains therein first diapers each having said waist's end portion lying on a side of said first surface of said package with respect to said crotch region's bottom, and second diapers each having said waist's end portion lying on a side of said second surface of said package opposed to said first surface with respect to said crotch region's bottom, so that said first and second diapers are alternately placed in close contact one with another to form a row in which the number of said first diapers is substantially equal to the number of said second diapers;

each of said diapers comprises a liquid-pervious topsheet facing a wearer's body, a liquid-impervious backsheet facing away from said wearer's body and a liquid-absorbent core interposed between said top- and backsheets and extending between said front and rear waist regions; and each of said diapers is further provided with a pair of second fold-guiding lines extending in said transversely opposite lateral portions in said longitudinal direction immediately outside transversely opposite side edges of said core so that said diaper is folded inwardly of said diaper at said transversely opposite lateral portions along said second fold-guiding lines.

2. A disposable diaper package, comprising a container and a plurality of pull-on disposable diapers contained in said container;

each of said diapers including front and rear regions and a crotch region between said front and rear regions, and comprising a liquid-pervious topsheet, a liquid-impervious backsheet and a liquid-absorbent core interposed between said topsheet and backsheet and extending between said front and rear regions, wherein transversely opposite lateral portions of the front and rear regions are attached to each other to form a waist hole and a pair of leg holes;

transversely opposite lateral portions of the crotch region and the liquid-absorbent core are folded inwardly of the diaper, along a pair of folding lines, respectively; and each of said folding lines has a V shape including two sections extending from an apex in a middle zone of said crotch region upwardly towards the front and rear regions, respectively, the apexes of the folding lines being spaced one from another in a transverse direction of the diaper so that the folding lines do not intersect or otherwise touch each other;

said diapers comprising first diapers having the waist holes lying adjacent a top of said container and second diapers having the waist holes lying adjacent a bottom of said container, wherein said first and second diapers are alternatingly placed one adjacent another to form at least one row of diapers in said container;

wherein each of said diapers is further folded inwardly along a pair of second folding lines, each of said second folding lines extending longitudinally in the transversely opposite lateral portions of the front and rear regions and being positioned outside transversely opposite side edges of said core.

3. A disposable diaper package, comprising a container and a plurality of disposable diapers contained in said container;

each of said diapers including front and rear regions and a crotch region between said front and rear regions, wherein transversely opposite lateral portions of the crotch region are folded along a pair of first folding lines and tucked inwardly of the diaper;

each of said folding lines including two sections extending from a middle zone of said crotch region upwardly towards the front and rear regions, respectively;

each of said diapers comprises a liquid-pervious topsheet, a liquid-impervious backsheet and a liquid-absorbent core interposed between said topsheet and backsheet and extending between said front and rear regions; and transversely opposite lateral portions of the front and rear regions of each of said diapers are folded along a pair of second folding lines and tucked inwardly of the diaper, each of said second folding lines extending longitudinally from the front to the rear regions and being positioned outside transversely opposite side edges of said core.

* * * * *